United States Patent [19]

Sato et al.

[11] Patent Number: 5,164,318

[45] Date of Patent: Nov. 17, 1992

[54] AUTOMATIC ENZYME IMMUNOASSAY ANALYZER

[75] Inventors: Takeshi Sato; Tomonori Mimura, both of Katsuta, Japan

[73] Assignee: Hitachi, Ltd., Tokyo, Japan

[21] Appl. No.: 613,979

[22] Filed: Nov. 15, 1990

Related U.S. Application Data

[63] Continuation of Ser. No. 100,369, Sep. 23, 1987, abandoned.

[30] Foreign Application Priority Data

Oct. 1, 1986 [JP] Japan .................. 61-233831

[51] Int. Cl.$^5$ .............................................. C12M 1/40
[52] U.S. Cl. .................... 435/288; 435/291; 435/808; 422/64; 422/100
[58] Field of Search ............. 435/7.92, 7.93, 7.94, 435/7.95, 174, 176, 177, 178, 180, 182, 287, 288, 289, 291, 312, 808, 809, 299-301; 436/501, 517, 518, 524, 527, 531, 535; 422/57, 58, 63, 64, 65, 100, 101

[56] References Cited

U.S. PATENT DOCUMENTS

| | | | |
|---|---|---|---|
| 4,039,652 | 8/1977 | Adams et al. | 424/1 |
| 4,276,051 | 6/1981 | Ginsberg et al. | 23/230 R |
| 4,837,159 | 6/1989 | Yamada | 422/64 |

FOREIGN PATENT DOCUMENTS

| | | | |
|---|---|---|---|
| 2448411 | 5/1975 | Fed. Rep. of Germany. | |
| 59-75154 | 4/1984 | Japan | 422/64 |

OTHER PUBLICATIONS

Enzyme Immunoassay, 2nd Edition, Chapter 3, pp. 30-49 Nov. 15, 1982.

*Primary Examiner*—Robert J. Warden
*Assistant Examiner*—William H. Beisner
*Attorney, Agent, or Firm*—Fay, Sharpe, Beall, Fagan, Minnich & McKee

[57] ABSTRACT

A sample containing a non-labeled antibody (or a non-labeled antigen) is drawn into a probe having contained therein an antigen (or an antibody) to which a labeled antibody (or a labeled antigen) is bound. A competitive reaction takes place in the probe. The amount of the non-labeled antibody (or the non-labeled antigen) is measured from the enzyme activity of the labeled antibody (or labeled antigen) in a reaction solution that is discharged from the probe into a cuvette.

5 Claims, 8 Drawing Sheets

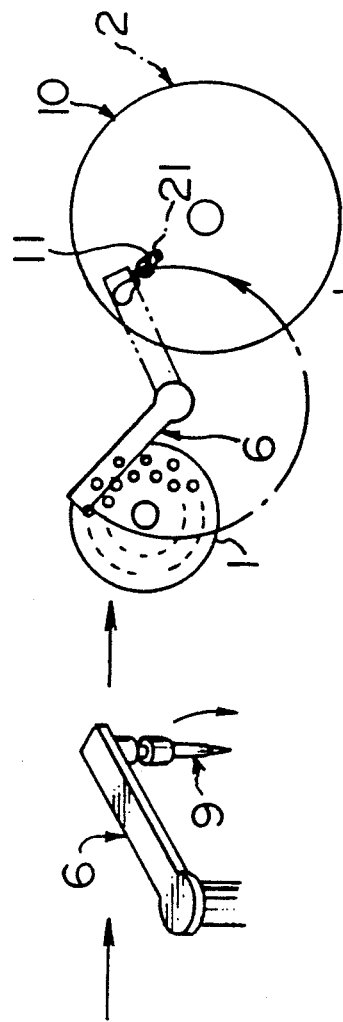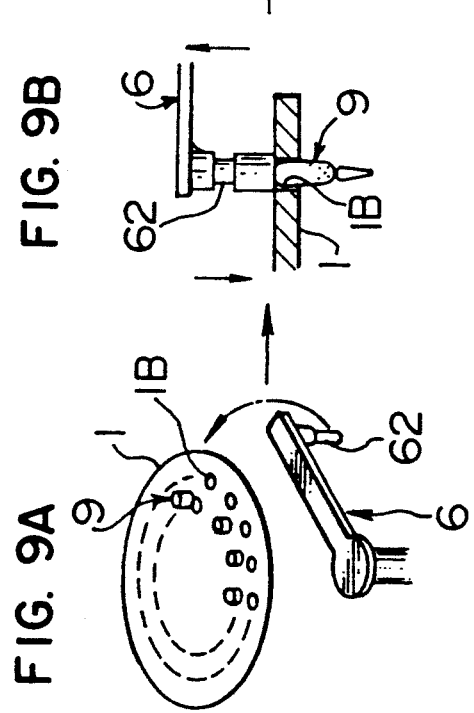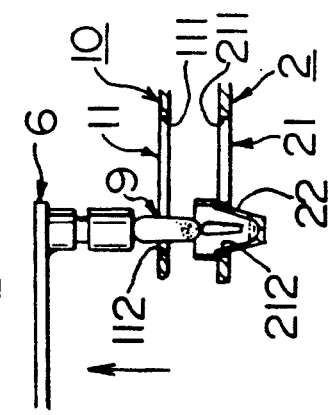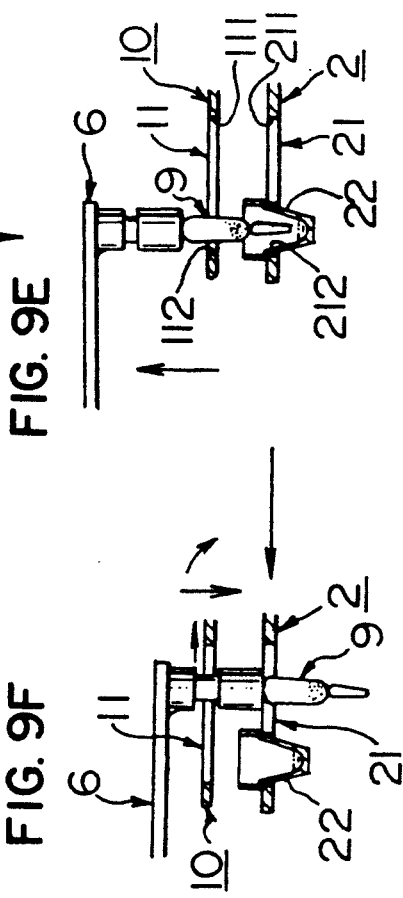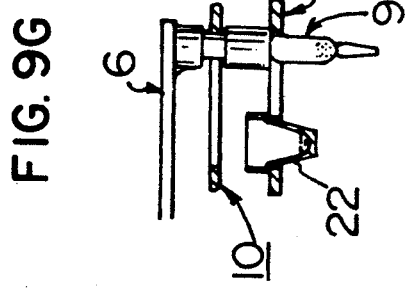

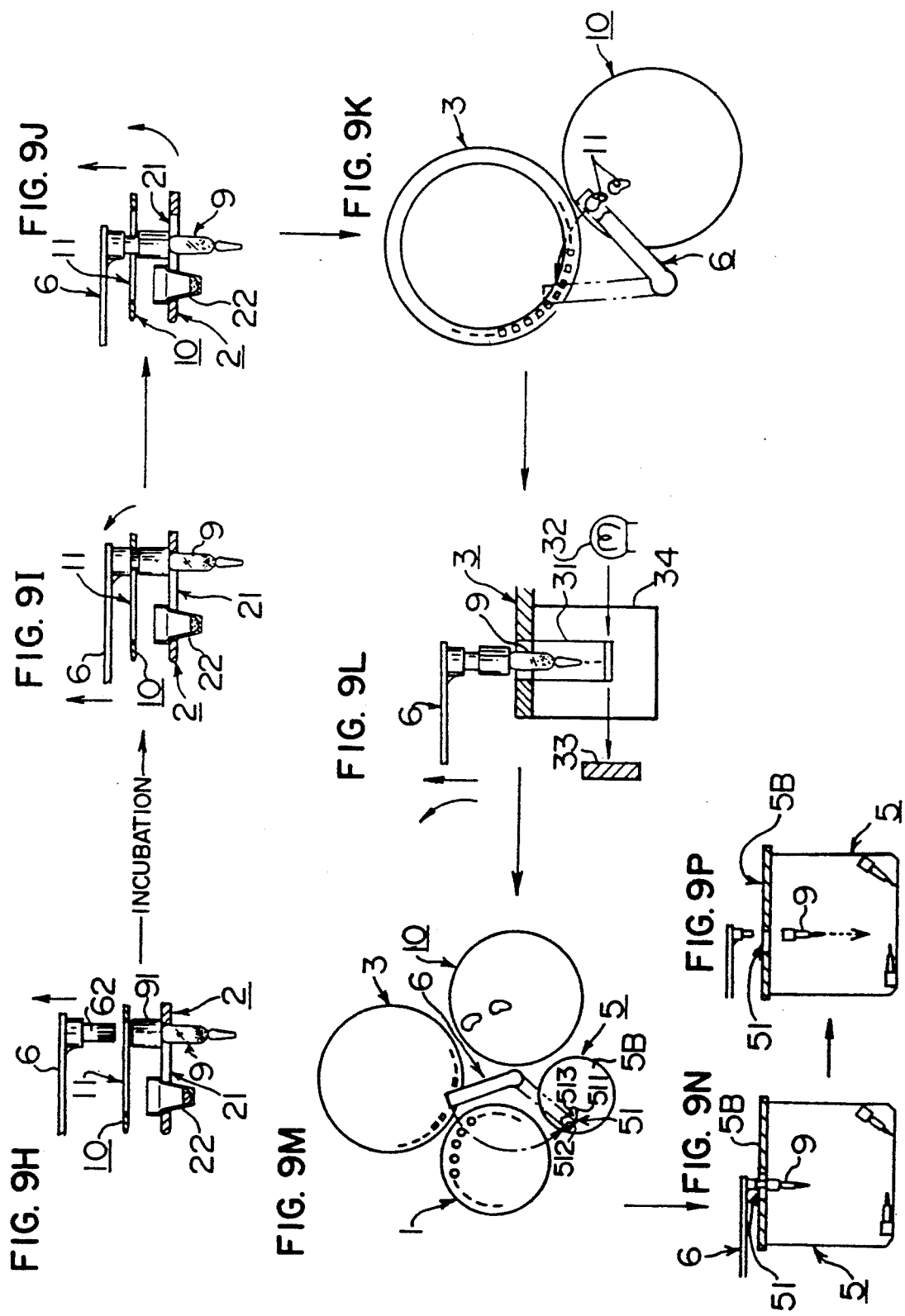

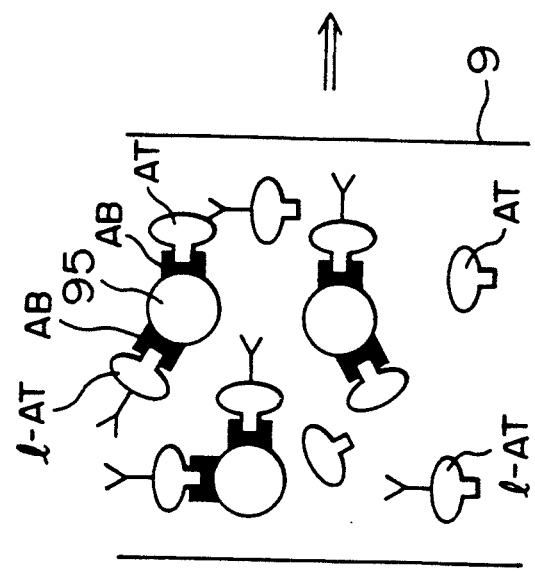
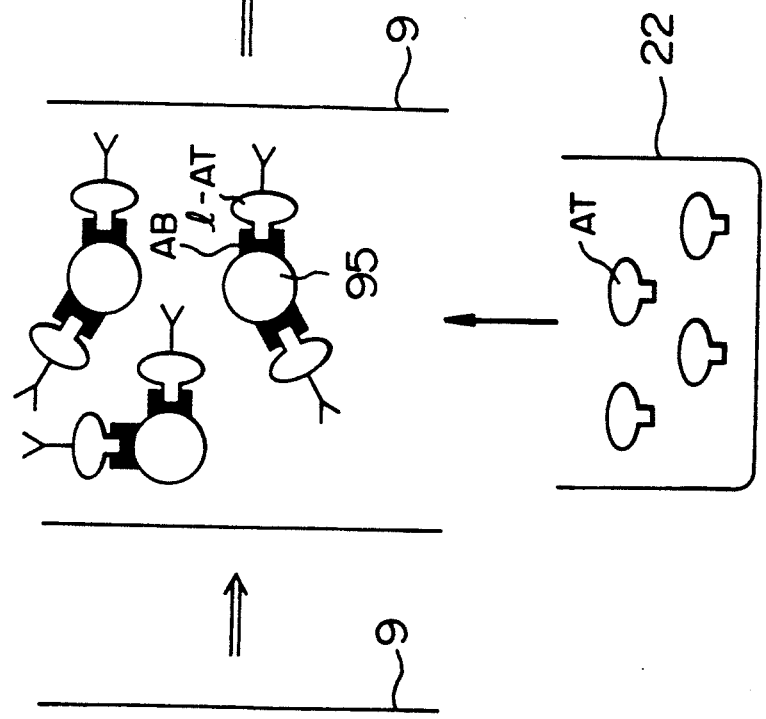
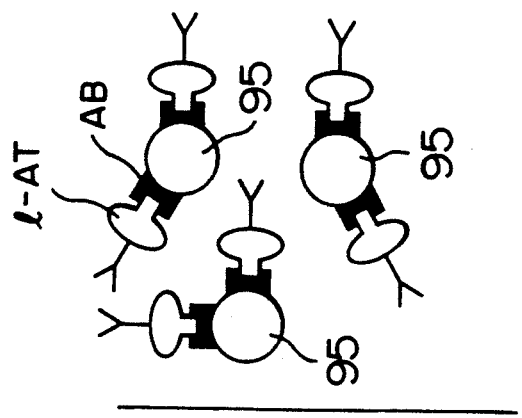

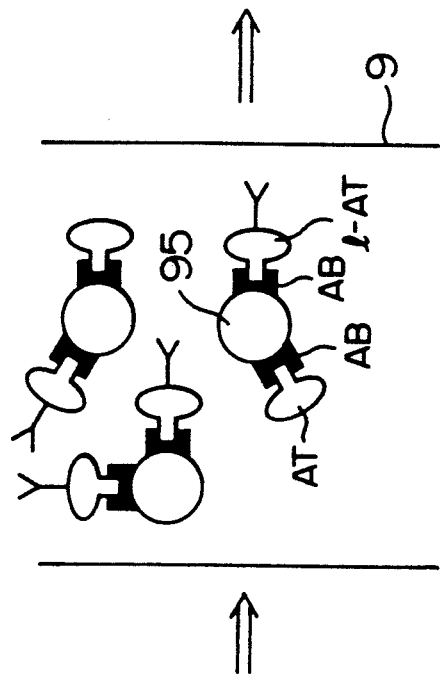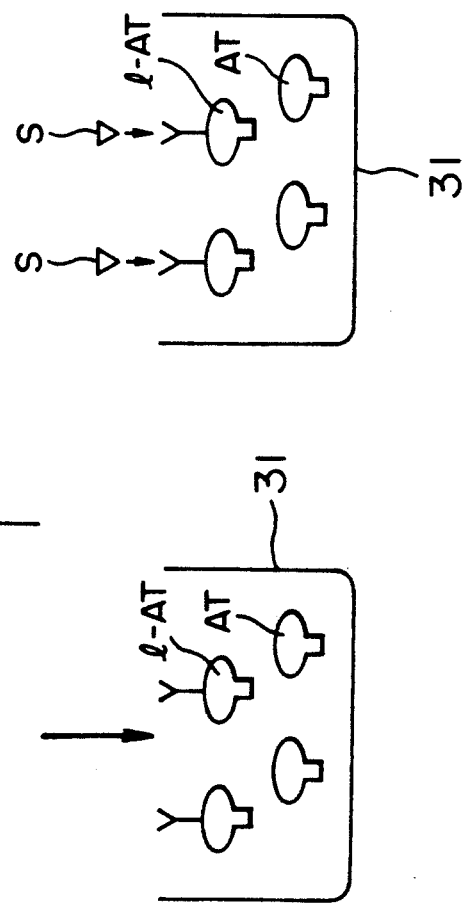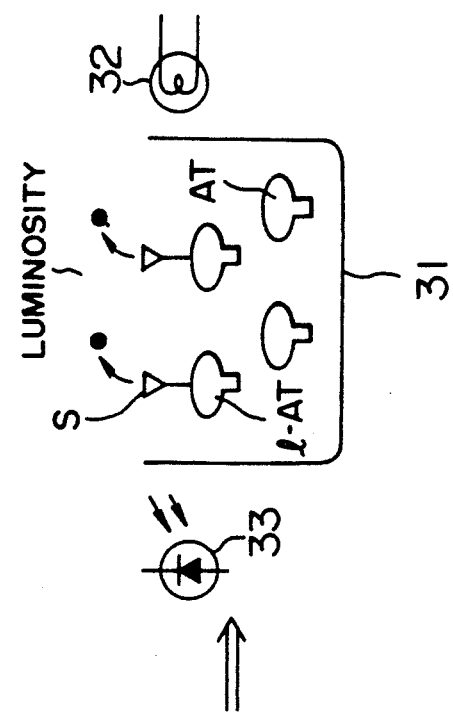

AUTOMATIC ENZYME IMMUNOASSAY ANALYZER

This application is a Continuation of application Ser. No. 100,369 filed Sep. 23, 1987, now abandoned.

FIELD OF THE INVENTION AND RELATED ART STATEMENT

The present invention relates to an enzyme immunoassay method requiring bound-free separation (B-F separation). The present invention also relates to an automatic analyzer using the enzyme immunoassay method.

As shown in "Enzyme immunoassay 2nd ed." pp. 30–49, B-F separation is a technique for measuring the activity of a label enzyme by physically separating a bound part (B) in which an antigen and an antibody are bound together and a free part (F) in which they are not bound as a result of antigen-antibody reaction, so as to measure the amount of the antigen (or antibody) in a sample. In B/F separation, however, a physical separating operation, i.e., centrifugal separation, and the removal of supernatant are troublesome and time-consuming. In addition, there has been delay in attempts to effect efficient and full-automatic measurement in comparison with items of biochemical analysis.

This B-F separation technique is effective since a scope of its application is wide, ranging from the low molecular weight to the high molecular weight. There are various methods of such separation, which will be described below.

1) Solid phase antibody method

First, an antibody is bound to a support and is kept in a solid phase. At this juncture, the biological activity of the antibody in a solid phase is maintained. As the support, there are cases where a test tube or the like is used and where a spherical or planar solid material is used. Subsequently, an enzyme-bound antigen (enzyme labelled antigen) is added. If the amount of the enzyme labelled antigen is made slightly greater than the amount of the antibody, a part of the antigen is bound to the antibody, while the other part remains unbound (free) with the antibody. At this juncture, the free part is in a solution, but since the bound part is adhered to the support, it is possible to separate these two parts by means of centrifugation, and the enzyme activity in either part is measured. At this juncture, if a non-labelled antigen is added, together with the predetermined amount of the labelled antigen, to the antibody, since the amount of the antibody is fixed, the amount of the labelled antigen bound to the antibody decreases by the amount of the non-labelled antigen which is bound to the antibody. Subsequently, the above-described operation is carried out by changing the amount of the non-labelled antigen, and the enzyme activity is measured. A calibration curve (reference curve) is prepared by plotting the amount of the non-labelled antigen (standard antigen) along the abscissa and the enzyme activity along the ordinate. Subsequently, a sample is added, instead of the standard antigen, to the antibody to take place an antigen-antibody reaction. In this state, if the enzyme activity is measured, the amount of antigen in the sample can be determined from the aforementioned calibration curve.

2) Double antibody method

In terms of its basic principle, this method also makes use of competitive reaction the same as the above-mentioned method does. However, the method of separation of a bound part and a free part differs. In this method, an antibody (a first antibody) is caused to react with an enzyme-labelled antigen in the state of a liquid phase. Since the separation between the liquid phase bound part and the liquid phase free part is difficult in this state, in order to make an aggregation, a predetermined amount of an antibody (a second antibody) which is capable of being bound to the first antibody is added, thereby producing the bound and free parts. Subsequently, they are separated into a sediment (a bound part) and a supernatant (a free part) by means of centrifugation. The other procedures are the same as those of the solid phase antibody method, and the amount of the antigen in a sample can be determined from a calibration curve.

3) Double antibody solid phase method

In this method, the second antibody is in a solid state, so that the bound and free parts can be readily separated from each other by means of light centrifugation or without any centrifugation. The other procedures are the same those of the double antibody method.

In the prior arts, the bound and the free parts are produced by the antigen-antibody reaction. Subsequently, only free part is removed out and then the enzyme activity in the bound part is measured.

With such a conventional technique, the removal of only the free part is time-consuming, so that automation has been difficult to achieve.

OBJECT AND SUMMARY OF THE INVENTION

Accordingly, a primary object of the present invention is to provide an improved enzyme immunoassay method which facilitates B-F separation and allows automation to be effected readily.

Another object of the present invention is to provide an automatic analyzer for carrying out such improved enzyme immunoassay method.

To this end, according to the present inventions, a sample including a non-labelled antibody (or a non-labelled antigen) to be measured is sucked into a sampling probe containing therein an antigen (or an antibody) to which a labelled antibody (or a labelled antigen) is bound, so as to take place a competitive reaction in the sampling probe. The amount of the non-labelled antibody (or the non-labelled antigen) to be measured is estimated by measuring an enzyme activity of the labelled antibody (or the labelled antigen) in a free part discharged into a cuvette from the sampling probe.

The above objects, features, and advantages of the present invention will become apparent from the following detailed description of the invention when read in conjunction with the accompanying drawings.

BRIEF DESCRIPTION OF THE DRAWINGS

FIGS. 9A to 9N and 9P are illustrations for explaining the operations of the analyzer shown in FIG. 1;

FIGS. 11A to 11F are illustrations for explaining the state of antigen-antibody reaction.

DETAILED DESCRIPTION OF THE PREFERRED EMBODIMENT

Figure 1:
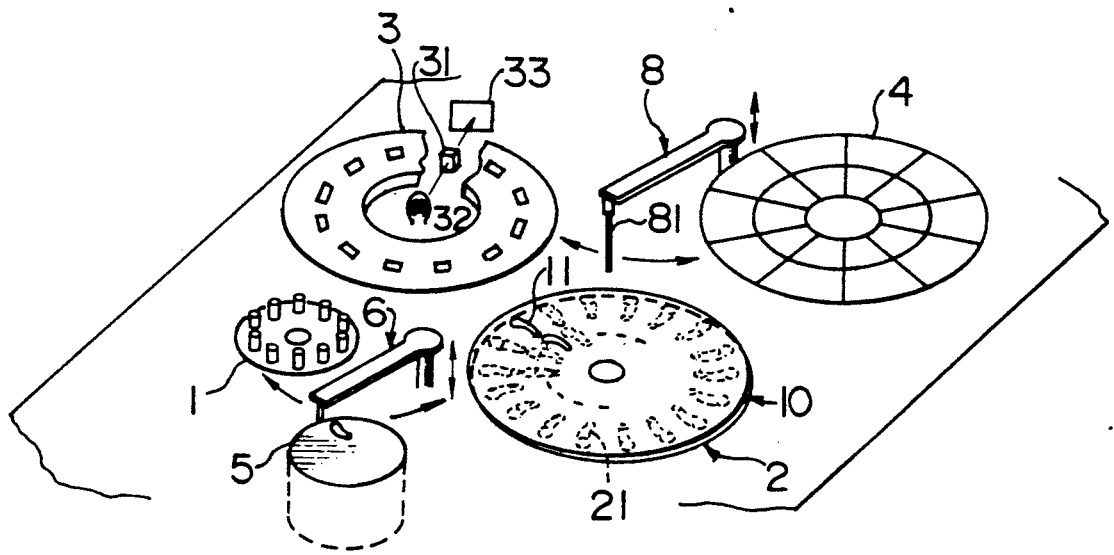
FIG. 1 is a perspective view showing an arrangement of analyzer according to a first embodiment of the present invention.

An automatic analyzer according to the embodiment of the present invention is designed to measure a very small amount of antigen in a serum sample, e.g. protein. As shown in FIG. 1, this automatic analyzer has a probe stock rotary disk 1, a sample carrying rotary disk 2, a reactor rotary disk 3, a reagent carrying rotary disk 4, and a probe disposal box 5, which are disposed in an interrelated manner. Furthermore, the automatic analyzer is provided with a probe carring arm means 6 which moves in a controlled manner, which will be described later, among the probe stock rotary disk 1, the sample carrying rotary disk 2, the reactor rotary disk 3, and the probe disposal box 5; a drive mechanism for driving the arm means 6; and a reagent carrying arm means 8 which reciprocates between the reactor rotary disk 3 and the reagent carrying rotary disk 4 and has a pipette 81.

Figure 2:
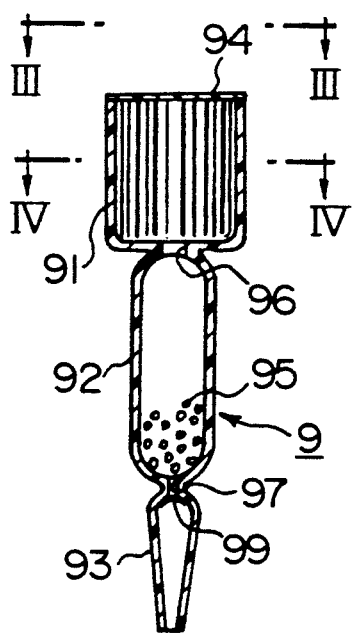
FIG. 2 is a enlarged cross-sectional view illustrating a probe shown in FIG. 1.
Figure 3:
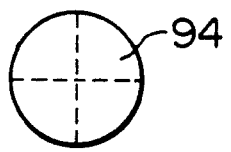
FIGS. 3 and 4 are cross-sectional views taken along the lines III—III and IV—IV of FIG. 2, respectively.
Figure 4:
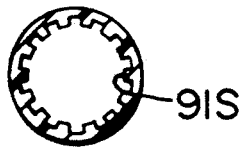

Referring to FIGS. 2 to 4, a hollow sampling probe 9 is shown, which is made of polypropylene and is to be placed on the probe stock rotary disk 1. This sampling probe 9 has a probe head 91, a probe body 92, and a tip 93. The probe head 91 is closed at an open end thereof by a thin seal 94 made of polypropylene and perforated in a cross shape. In addition, this probe head 91 has an outer diameter greater than that of the probe body 92 and a serrated inner peripheral surface 91S. The probe body 92 accommodates therein a multiplicity of microparticles 95 made of a resin. An antibody complementary with the aforementioned antigen is physically or chemically bound to the surfaces of the microparticles 95, as will be described later. The probe body 92 is connected at one end thereof to the probe head 91 through a reduced-diameter neck portion 96 so as to prevent the evaporation of the sample, and at the other end thereof to the tip 93 which has an outer diameter smaller than that of the probe body 92 through a reduced-diameter neck portion 97 so as to prevent the leak of the sample. The reference numeral 99 denotes a net provided for preventing the particles 95 from dropping from the probe 9. When the particles 95 have a dimension larger than that of the neck portion 97, the net 99 is not necessary for this purpose.

The binding of the antibody to the surfaces of the resin particles is effected by, for instance, physical adsorption. For example, the antibody is diluted with a carbonic acid-dicarbonic acid buffer solution (0.05M, pH 9.6) to 1–10 μg/ml. The resin particles are immersed in this diluent and are allowed to stand for 24 hours at 4° C. or for two hours at room temperature so as to allow the antibody to be adsorbed by the resin surfaces. Thereafter, the enzyme-labelled cognate antigen is bound on the adsorbed antibody.

Figure 5:
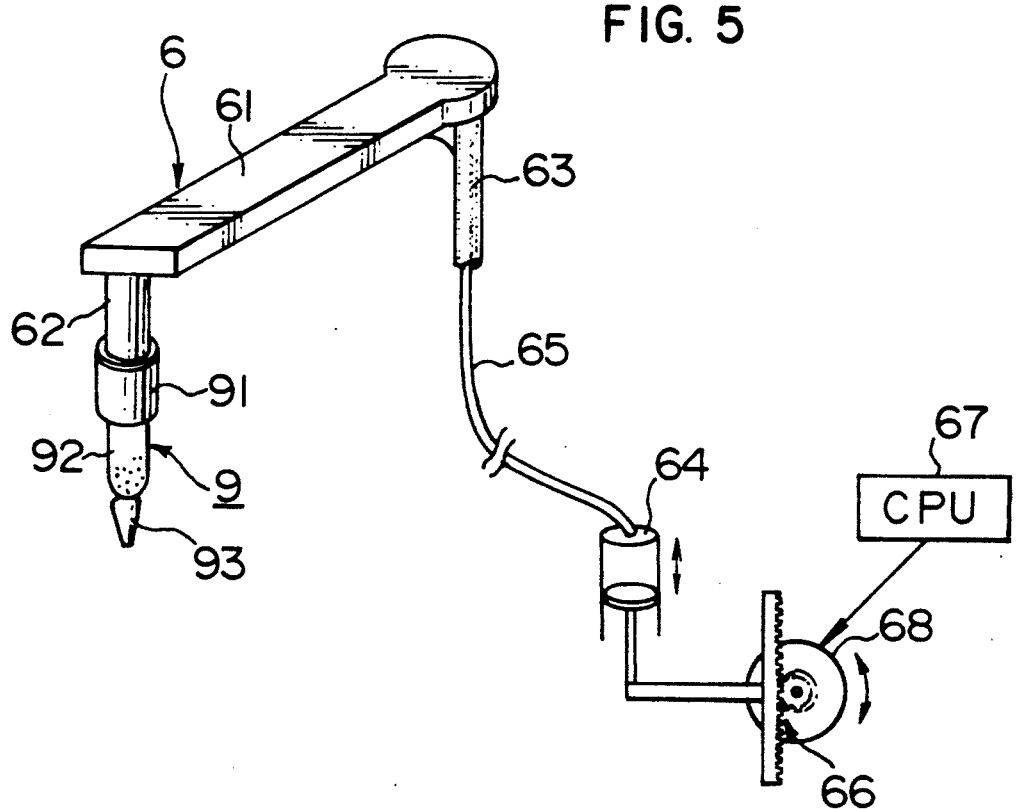
FIG. 5 is a perspective view illustrating a probe carrying arm means and a piston driving mechanism.
Figure 12:
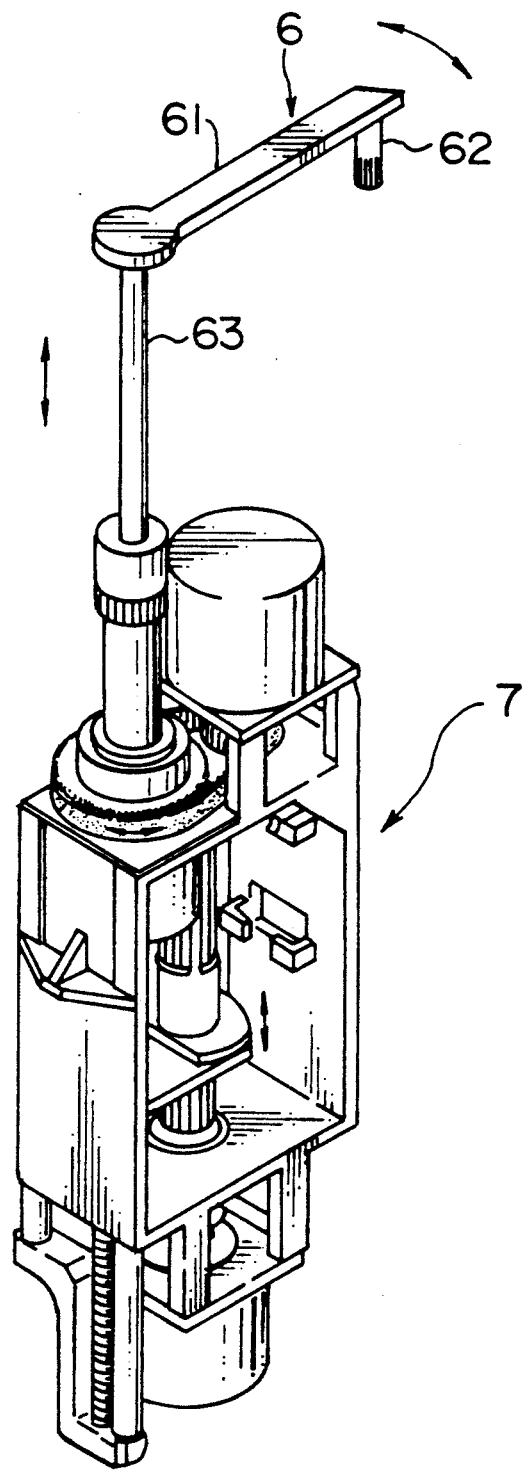
FIG. 12 is a perspective view showing a drive mechanism for the probe carrying arm means.

FIG. 5 illustrates in detail the probe carrying arm means 6. The probe carrying arm means 6 has an arm 61, an carrying tube 62 provided at one end of the arm 61, and a swing axle 63 provided at the other end of the arm 61. The probe carrying arm means 6 is swingable about the axis of the swing axle 63 by means of a belt drive mechanism of a drive mechanism 7 (FIG. 12) driven by a pulse motor, and is movable in the axial direction of the swing axle 63 through a spline shaft drive by a pulse motor of the drive mechanism 7. The carrying tube 62 has an outer diameter which closely fits with the serrated inner surface 91S of the probe head 91, and then is capable of communicating with the inside of the probe body 92 when engaged therewith. In addition, the carrying tube 62 communicates with a piston-cylinder apparatus 64 through a passage 65 extending through the arm 61 and the swing axle 63. The sample can be sucked into or discharged from the probe body 92 by driving the piston-cylinder apparatus 64 by means of a pulse motor 68 and a rack and pinion mechanism 66. The driving of the pulse motors for the probe carrying arm means 6 and the piston-cylinder apparatus 64 is controlled by a CPU 67.

Figure 6:
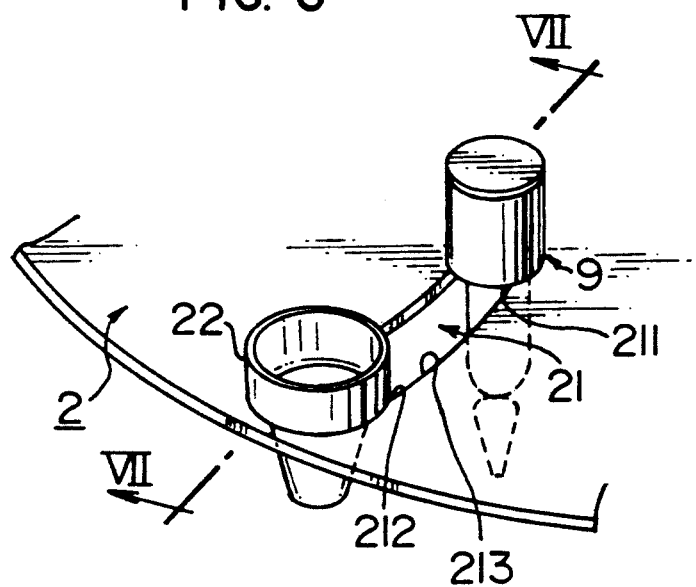
FIG. 6 is a perspective view illustrating a probe 9 and a sample cup 22 both disposed on a sample carrying rotary disk.
Figure 7:
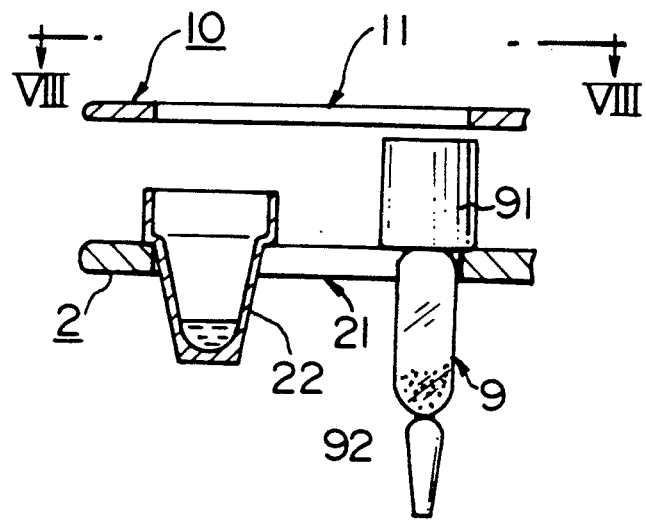
FIG. 7 is a cross-sectional view taken along the line VII—VII of FIG. 6.
Figure 8:
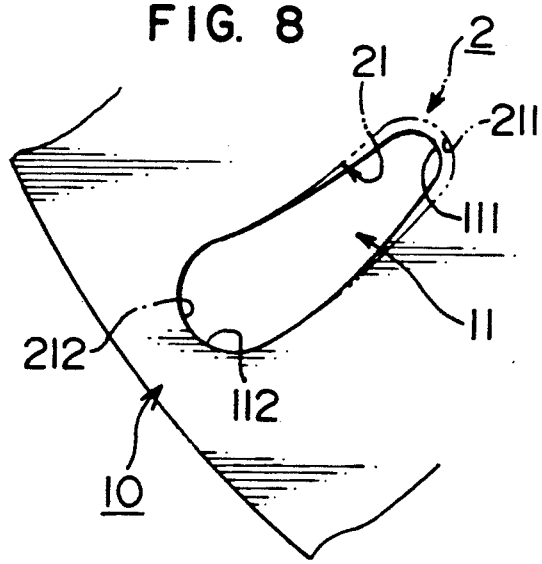
FIG. 8 is a top plan view taken along the line VIII—VIII of FIG. 7.

Referring now to FIGS. 6 to 8, the detailed description will be made of the arrangement of the sample carrying rotary disk 2. A plurality of openings 21 are formed concentrically in the sample carrying rotary disc 2 (only one is shown in FIG. 6). Each of the openings 21 is constituted by a smaller partial circular bore 211 having a diameter which is smaller than the outer diameter of the probe head 91 and greater than the outer diameter of the probe body 92, a larger partial circular bore 212 disposed radially outwardly of the bore 211 and having a diameter which is smaller than the outer diameter of a large-diameter portion of a sample cup 22 which accommodates the sample and greater than the outer diameter of the probe head 91, and an arcuate slit 213 connecting the bores 211, 212 and having the same swinging curvature as that of the arm 61. Accordingly, the sampling probe 9 and the sample cup 22 can be placed on the disk 2 at the bores 211, 212, respectively. A cover disk 10 is disposed above the sample carrying rotary disk 2 in such a manner as to provide a gap of about 1 mm between a top end of the probe head 91 of the probe 9 rested on the disk 2 and the lower surface of the cover disk 10. This cover disk 10 has an outer diameter substantially equal to that of the sample carrying rotary disk 2 and is stationary. Two openings 11 of the substantially same configuration as that of the opening 21 are formed radially in tandem at the portions of the cover disk 10 opposing the opening 21 of the sample carrying rotary disk 2. In other words, the arrangement is such that the diameter of the larger partial circular bore 112 of the opening 11 opposing the larger partial circular bore 212 of the opening 21 is equal to the diameter of the larger partial circular bore 212, whereas the diameter of the smaller partial circular bore 111 of the opening 11 opposing the smaller partial circular bore 211 of the opening 21 is greater than the outer diameter of the carrying tube 62 but smaller than the outer diameter of the probe head 91.

Referring now to FIGS. 9A to 9N and 9P, the description will be made of the operation of this automatic analyzer.

Step 1 (FIG. 9A)

First, the probe carrying arm means 6 is swung to above the probe stock rotary disk 1 by means of the drive mechanism 7. A plurality of bores 1B are disposed concentrically in the probe stock rotary disk 1, each of which has a diameter smaller than the outer diameter of the probe head 91 and greater than the outer diameter of the probe body 92. A plurality of sampling probes 9 are placed on the probe stock rotary disk 1 via the bores 1B. The swing movement of the probe carrying arm means 6 stops temporarily when the carrying tube 62 of the probe carrying arm means 6 has arrived at a position above the probe 9 disposed on the probe stock rotary disk 1.

Step 2 (FIG. 9B)

Next, the probe carrying arm means 6 is lowered by the drive mechanism 7. The carrying tube 62 enters the probe head 91 by tearing the seal 94 provided on the probe head 91 into four leaflets, and is closely fitted with the serrated inner surface 91S. Thus the probe 9 is connected to the probe carrying arm means 6. Subsequently, the probe carrying arm means 6 stops temporarily.

Step 3 (FIG. 9C)

The probe carrying arm means 6 is then raised by the drive mechanism 7. Consequently, the probe 9 is also raised together with the probe carrying arm means 6. Since the diameter of the bore 1B of the probe stock rotary disk 1 is greater than the outer diameter of the probe body 92, the probe 9 can be removed easily from the probe stock rotary disk 1. Subsequently, the arm means 6 is swung toward the sample carrying rotary disk 2.

Step 4 (FIG. 9D)

The probe carrying arm means 6 stops temporarily when the sampling probe 9 has arrived at a position above the larger partial circular bore 112 of the opening 11 in the cover disk 10. The sample cup 22 is positioned in the larger partial circular bore 212 provided in the sample carrying rotary disc 2 below the larger partial circular bore 112. The probe carrying arm means 6 is then lowered down to a position at which the tip 93 of the sampling probe 9 enters a serum sample in the sample cup 22. Consequently, the serum sample can be sucked into the probe 9.

Step 5 (FIG. 9E)

The piston-cylinder apparatus 64 then operates, and the serum sample is sucked into the probe body 92 of the sample probe 9.

Step 6 (FIG. 9F)

After sucking, the arm means 6 is raised to a position at which the sampling probe 9 is removed from the sample cup 22. Furthermore, the arm means 6 is swung toward the smaller partial circular bore 111 through the opening 11 in the cover disk 10, i.e., toward a central portion thereof, to a position at which the sampling probe 9 is completely disengaged from the sample cup 22. The arm means 6 stops temporarily at the position and is then lowered until the top end of the probe head 91 of the probe 9 is lowered slightly below the underside of the cover disk 10.

Step 7 (FIG. 9G)

The probe carrying arm means 6 is swung in such a manner as to move toward the smaller partial circular bore 211 through the opening 21. When the sampling probe 9 arrives at the smaller partial circular bore 211, the movement of the probe carrying arm means 6 is stopped.

Step 8 (FIG. 9H)

Subsequently, the probe carrying arm means 6 is raised. At that juncture, since the diameter of the smaller partial circular bore 111 of the opening 11 in the cover disk 10 is smaller than that of the probe head 91, the sampling probe head 91 against the cover disk 10 and separates from the carrying tube 62 of the probe carrying arm means 6, to remain on the sample carrying rotary disk 2. At that juncture, the four leaflets of the seal 94 bent inwardly by the carrying tube 62 return to their original states by virtue of their resiliency, thereby closing the probe head 91.

Step 9 (FIG. 9I)

The sampling probe 9 is subjected to incubation for a predetermined time duration to effect an immunoreaction. The enzyme-labelled antigen (l-AT) is bound to the solid phase antibody (AB) bound to the surfaces of the resin particles (see FIG. 11A). Accordingly, the competitive immunoreaction takes place during incubation between the non-labelled antigen (AT) in the sample sucked into the probe 9 in Step 5 and the enzyme-labelled antigen (l-AT) (see FIG. 11B). In consequence, the non-labelled antigen (AT) and the enzyme-labelled antigen (l-AT) are included in the free part (see FIG. 11C). After incubation, the probe carrying arm means 6 is moved in such a manner that the carrying tube 62 is again located above the sampling probe 9. Subsequently, the probe carrying arm means 6 is lowered and the carrying tube 62 is closely fitted with the probe head 91 to again connect the sampling probe 9 to the probe carrying arm means 6.

Step 10 (FIG. 9J)

The probe carrying arm means 6 is swung at a constant level in such a manner that the sampling probe 9 returns towards the sample cup 22 through the opening 21 in the sample carrying rotary disk 2. The probe carrying arm means 6 stops its movement before the sampling probe 9 is brought into contact with the sample cup 22.

Step 11 (FIG. 9K)

The probe carrying arm means 6 is raised, and stops its upward movement when the tip 93 of the sampling probe 9 is completely disengaged from the cover disk 10.

Step 12 (FIG. 9L)

The probe carrying arm means 6 is swung toward the reactor disk 3, and is stopped when the sampling probe 9 has arrived at a position above a cuvette 31 in a thermostatic bath 34 in the reactor disk 3. Subsequently, the probe carrying arm means 6 is lowered down to a position at which a certain gap is provided between the tip 93 of the sampling probe 9 and the bottom of the cuvette 31, and the probe carrying arm means 6 is then stopped temporarily. Subsequently, the piston-cylinder apparatus 64 is driven to discharge the free part from the probe body 92 into the cuvette 31 (FIG. 11D).

Step 13 (FIG. 9M)

The probe carrying arm means 6 is raised in such a manner that the tip 93 of the sampling probe 9 is located above the reactor disc 3. Subsequently, the probe carrying arm means 6 is swung toward the probe disposal box 5, and is stopped above an opening 51 formed in the cover 5B on the probe disposal box 5. The opening 51 has a smaller partial circular bore 511 having a diameter which is smaller than the outer diameter of the probe head 91 and greater than the outer diameter of the carrying tube 62, a larger partial circular bore 512 disposed radially outwardly of the bore 511 and having a diameter greater than the outer diameter of the probe head 91, and an arcuate slit 513 connecting these bores 511, 512 and having the same curvature as the swing curvature of the arm 61. The probe carrying arm means 6 is lowered in such a manner that the sampling probe 9 passes through the larger partial circular bore 512, and is stopped when the top end of the probe head 91 is lowered below the underside of the cover 5B.

Step 14 (FIGS. 9N and 9P)

The probe carrying arm means 6 through the slit 513 is swung in such a manner that the sampling probe 9 moves toward the smaller partial circular bore 511 through the slit 513. The probe carrying arm means 6 is stopped temporarily when the sampling probe 9 has arrived at the smaller partial circular bore 511, and thereafter the probe carrying arm means 6 is raised. At that juncture, since the diameter of the smaller partial circular bore 511 is smaller than the outer diameter of the probe head 91, the sampling probe 9 is abutted against the probe disposal box cover 5B. The sampling probe 9 is separated from the carrying tube 62 of the probe carrying arm means 6, and then drops into the probe disposal box 5.

Step 15

The reagent carrying arm means 8 reciprocates between the reagent carrying rotary disk 4 and the reactor disk 3 so as to pipette a specific substrate (S) in the reagent carrying rotary disk 4 into the cuvette 31 in the reactor disk 3. Consequently, the substrate is added to the free part in the cuvette 31 to start the enzyme reaction (FIG. 11E). Subsequently, the cuvette 31 is moved to a measurement position by the rotation of the reactor disk 3. The absorbance of the free part in the cuvette 31 is measured by using a light source 32 and a spectrophotometer 33 (FIG. 11F). It is possible to determine the amount of protein contained in the serum sample from the measured absorbance by referring to a calibration curve.

The foregoing Steps 1 to 15 are repeatedly carried out in a controlled manner by the aforementioned CPU 67.

The above embodiment relates to an automatic analyzer used in the measurement of an antigen. However, in the above embodiment, it is possible to measure an antibody by replacing the antigen with the antibody.

Figure 10:
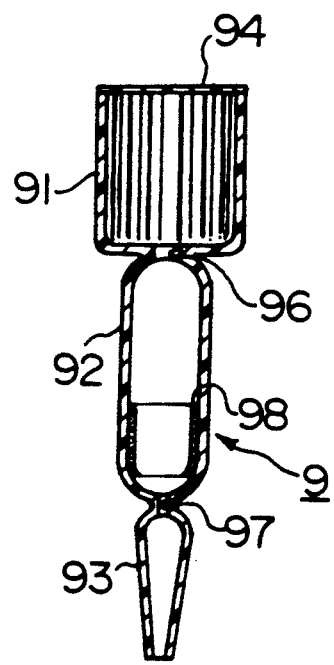
FIG. 10 is a cross-sectional view illustrating a modification of the probe.

In addition, instead of causing the antigen (or antibody) to be bound to the surfaces of the resin particles, an arrangement may be provided alternatively in which an inner surface of the resin-made probe body is coated directly with an antigen (or antibody) layer 98, as shown in FIG. 10.

Hereafter, comparison will be made between conventional analysis and analysis based on the apparatus in accordance with the present invention.

Example 1) Measurement of ferritin

Labelle enzyme: $\beta$-D-galactosidase

Measuring method: 0.15 ml of a reagent containing $1 \times 10^{-4}$M4-methylumbelliferyl-$\beta$-D-galactoside in a buffer solution A* is added to a sample in a cuvette after B/F separation. During the incubation for 10 minutes at 37° C., the fluorescence (450 nm, excitation: 360 nm) is measured.

Buffer solution A*: A 0.01M sodium phosphate buffer solution (pH 7.0) containing 0.1% BSA-0.1M NaCl-1 mM MGCl$_2$-0.1% NaN$_3$.

|  | Conventional unautomated case | This Embodiment |
| --- | --- | --- |
| Immunoassay reaction | 6 hr. | 30 min. |
| Removal of supernatant by centrifugation | 20–30 min. | — |
| Measurement of enzyme activity | 20 min. | 10 min. |

Buffer solution A*: A 0.01M sodium phosphate buffer solution (pH 7.0) containing 0.1% BSA - 0.1M NaCl - 1 mM MgCl$_2$ - 0.1% NaN$_3$.

Example 2) Measurement of insulin

Labelle enzyme: $\beta$-D-galactosidase

Measuring method: 0.1 ml of a 0.05M phosphoric acid buffer solution (pH 7.3) is added to a cuvette which contains a sample after B/F separation. The mixture is then allowed to incubate for 3 minutes at 37° C. Further, 0.1 ml of a substrate solution [obtained by dissolving 0.06 g of 0-nitrophenyl-$\beta$-D-galactoside in 100 ml of a 0.05M phosphoric acid buffer solution (pH 7.3)] is added to it. During the incubation for 10 minutes at 37° C., the absorbance at 420 nm is measured.

|  | Conventional unautomated case | This Embodiment |
| --- | --- | --- |
| Immunoassay reaction | 3 hr. | 30 min. |
| Removal of supernatant by centrifugation | 20–30 min. | — |
| Measurement of enzyme activity | 90 min. | 20 min. |

Example 3) Measurement of cortisol

Labelle enzyme: Alkaline phosphatase

Measuring method: 0.1 ml of a substrate solution [obtained by dissolving 0.215 g of phenyl phosphate disodium and 0.09 g of 4-aminoantipyrine in 200 ml of a 0.05M sodium hydrogencarbonate buffer solution (pH 10.5)] is added to a sample (in a cuvette) after B/F separtion. After the mixture is allowed to incubate for 30 minutes at 37° C., and 0.1 ml of a coloring solution (obtained by dissolving 0.38 g of potassium ferricyanide in 200 ml of a 0.2M boric acid solution). Then, the absorbance is measured at 500 nm for 10 minutes.

|  | Conventional unautomated case | This Embodiment |
| --- | --- | --- |
| Immunoassay reaction | 24 hr. (double antibody method) | 40 min. |
| Removal of supernatant by centrifugation | 20–30 min. | — |

-continued

|  | Conventional unautomated case | This Embodiment |
| --- | --- | --- |
| Measurement of enzyme activity | 90 min. | 40 min. |

Example 4) Measurement of prostaglandin (PGF2α)
Labelle enzyme: β-D-galactosidase
Measuring method: 0.3 ml of a substrate solution (obtained by adding to 50 ml of a buffer solution B* 0.34 ml of a mixture in which 4-methylumbelliferyl-D-galactoside is dissolved in N,N'-dimethylformamide in such a manner that its ultimate concentration is 14.7 mM) is added to a sample in a cuvette after B/F separation. During the incubation for 20 minutes at 37° C., the fluorescence is measured (450 nm, excitation: 360 nm).

Buffer solution B*: A buffer solution in which 0.1M NaCl, 1 mM MgCl$_2$, 0.1% NaN$_3$, and 0.1% egg albumin are contained in a 10 mM sodium phosphate solution (pH 7.0).

|  | Conventional unautomated case | This Embodiment |
| --- | --- | --- |
| Immunoassay reaction | 24 hr. (double antibody method) | 40 min. |
| Removal of supernatant by centrifugation | 20-30 min. | — |
| Measurement of enzyme activity | 90 min. | 40 min. |

Buffer solution B*: A buffer solution in which 0.1M NaCl, 1 mM MgCl$_2$, 0.1% NaN$_3$, and 0.1% egg albumin are contained in a 10 mM sodium phosphate solution (pH 7.0).

Example 5) Measurement of α-fetoprotein
Labelle enzyme: Peroxidase
Measuring method: 0.25 ml of a substrate solution [obtained by dissolving 0-phenylenediamine in a citrate buffer solution (containing 0.1M citric acid —0.2M Na$_2$HPO$_4$ (pH 5.5), 0.02% H$_2$O$_2$, and 0.01% thimerosal) at a ratio of 3 mg/ml] is added to a sample in a cuvette after B/F separation. During the incubation for 10 minutes at 37° C., the absorbance at 492 mm is measured.

|  | Conventional unautomated case | This Embodiment |
| --- | --- | --- |
| Immunoassay reaction | 24 hr. (double antibody method) | 40 min. |
| Removal of supernatant by centrifugation | 20 min. | — |
| Measurement of enzyme activity | 10-30 min. | 10 min. |

What is claimed is:

1. An automatic analyzer for performing enzyme immunoassays, comprising:
   a probe stock rotary disk supporting rotation of a plurality of hollow sampling probes;
   each of said sampling probes having a head and a body portion, said body portion being provided in an interior thereof with a specific antigen or a specific antibody bound to an enzyme-labelled cognate antibody or an enzyme-labelled cognate antigen, respectively;
   a probe carrying arm means to which each said sampling probe is detachably connectable, said arm means including a carrying tube for connecting said arm means to said head and providing fluid communication therewith;
   said sampling probes having sealing means for sealing the connection between said carrying tube and said head and for sealing said head upon separation of said carrying tube from said head;
   a sample carrying rotary disk supporting rotation of a plurality of sample cups containing a sample which includes a non-labelled complementary antibody or a non-labelled complementary antigen;
   a reactor rotary disk supporting rotation of a plurality of cuvettes;
   said probe carrying arm means including means for introducing a predetermined amount of a sample from said plurality of sample cups into the interior of one of said sampling probes so as to allow a competitive immunoreaction to take place therein, and for discharging a reaction solution from said one sampling probe into one of said cuvettes on said reactor rotary disk;
   means for adding a predetermined amount of a substrate into said one cuvette;
   means for measuring enzyme activity of said sample in said one cuvette;
   means for driving said probe carrying arm means for carrying one of said sampling probes among said probe stock rotary disk, said sample carrying rotary disk and said reactor rotary disk;
   means for controlling the movement of said driving means for said probe carrying arm means, said probe stock rotary disk, said sample carrying rotary disk, and said reactor rotary disk in a controlled, synchronized manner;
   said sample carrying rotary disk having openings;
   a cover disk mounted above said sample carrying rotary disk having openings therein aligned with said openings in said sample carrying rotary disk, said sample carrying rotary disk openings receiving said sample cups and said probes when detached from said carrying tube; and
   said cover disk openings having a first portion for permitting said probes to pass through said cover disk openings to be received in said sample carrying rotary disk openings, and said cover disk openings having a second portion spaced from said first portion having a dimension smaller than a dimension of said head of said probes for preventing upward movement of said probe as said arm means moves upwardly from said cover disk to detach said connecting tube from said head.

2. An automatic analyzer according to claim 1, further comprising:
   said probe carrying arm means being pivotally mounted to swing through a curved path when carrying said probes, and said openings of said cover disk having an arcuate shaped through portion extending between said first and second portions that corresponds in shape to an arcuate portion of said curved path followed by said arm means.

3. An automatic analyzer for performing enzyme immunoassays, comprising:

a probe stock rotary disk supporting rotation of a plurality of hollow sampling probes each of said hollow sampling probes having a head and a body portion with an interior;

a probe carrying arm means for detachably connecting to said probes, said arm means including carrying tube means for connecting said arm means to said head of said probes to provide fluid communication therewith;

a sample carrying rotary disk supporting rotation of a plurality of sample cups for containing a sample;

a reactor rotary disk supporting rotation of a plurality of cuvettes;

said probe carrying arm means including means for introducing a predetermined amount of a sample from one of said sample cups into the interior of said sampling probes to allow a competitive immunoreaction to take place therein, and for discharging a reaction solution from said sampling probes into one of said cuvettes on said reactor rotary disk;

means for adding a predetermined amount of a substrate into said one cuvette;

means for measuring enzyme activity of said sample in said one cuvette;

means for driving said probe carrying arm means for carrying one of said sampling probes in a curved path among said probe stock rotary disk, said sample carrying rotary disk and said reactor rotary disk;

means or controlling the movement of said probe stock rotary disk, said sample carrying rotary disk, said reactor rotary disk, and said driving means for said probe carrying arm means to synchronize movement of said arm means and said disks;

a cover disk mounted above said sample carrying rotary disk, each of said sample carrying rotary disk and cover disk having aligned openings therethrough;

said openings of said sample carrying rotary disk receiving said sample cups and said probes; and said openings of said cover disk having a first portion permitting one of said probes to pass through said cover disk so that said one probe is received within an aligned one of said openings of said sample carrying rotary disk, and a second portion spaced from said first portion having a dimension smaller than a dimension of said head of said one probe for holding said one probe in said aligned opening of said sample disk when said arm means is driven upwardly from said cover disk by said driving means to detach said carrying tube means from said probe head.

4. An automatic analyzer according to claim 3, further comprising sealing means for sealing the connection between said carrying tube and said head and for sealing said head of said probe upon separation of said carrying tube from said head.

5. An automatic analyzer according to claim 3, wherein said first and second portions of said openings in said over disk are each a circular bore spaced from one another; and said probe body portion having a substantially cylindrical outer surface, said head of said probes being received within said opening of said sample carrying rotary disk beneath said circular bore of said second portion of said cover disk opening, wherein said arm means carrying said one probe passes said one probe through said first portion of said opening in said cover disk, so that it is seated within said sample disk opening and then moves said one probe to a position beneath said second portion of said cover disk opening so that said head of said one probe is positioned beneath said second portion to prevent upward movement of said one probe in an upward direction perpendicular to said cover disk for detaching said carrying tube from said head of said one probe when said arm means is driven in said upward direction.

* * * * *